United States Patent [19]

Ogino et al.

[11] Patent Number: 4,478,734
[45] Date of Patent: Oct. 23, 1984

[54] DETERGENT COMPOSITION COMPRISING A MIXTURE OF AN N-ACYLLYSINE AND ANIONIC SURFACE ACTIVE AGENTS, POSSESSING UNIQUE PROPERTIES IN SOFT AND HARD WATER

[75] Inventors: Keizo Ogino, Tokyo; Masahiro Takehara; Takeshi Miyoshi, both of Fujisawa; Koichiro Sagawa, Kawasaki, all of Japan

[73] Assignee: Ajinomoto Company Incorporated, Tokyo, Japan

[21] Appl. No.: 478,669

[22] Filed: Mar. 25, 1983

[30] Foreign Application Priority Data

Apr. 2, 1982 [JP] Japan ................... 57-55074

[51] Int. Cl.$^3$ .................... C11D 1/10; C11D 7/50
[52] U.S. Cl. .................... 252/117; 252/526; 252/527; 252/545; 252/546; 252/550; 252/551; 252/555; 252/558; 252/DIG. 13; 260/404.5
[58] Field of Search ............. 252/117, 546, 527, 550, 252/551, 555, 558, DIG. 13; 260/404.5 A, 404.5 PA

[56] References Cited

U.S. PATENT DOCUMENTS

| | | |
|---|---|---|
| 3,683,019 | 8/1972 | Wakamatsu et al. ......... 260/404.5 X |
| 3,707,505 | 12/1972 | Maeda et al. .................. 252/136 |
| 4,166,048 | 8/1979 | Nishimura et al. ............. 252/546 |
| 4,246,131 | 1/1981 | Lohr ................................ 252/153 |
| 4,374,056 | 2/1983 | Watanabe et al. .............. 252/546 |
| 4,375,421 | 3/1983 | Rubin et al. .................... 252/110 |

FOREIGN PATENT DOCUMENTS

| | | |
|---|---|---|
| 11926 | 7/1967 | Japan . |
| 10921 | 4/1973 | Japan . |
| 16599 | 2/1981 | Japan . |
| 53196 | 5/1981 | Japan . |

*Primary Examiner*—Prince E. Willis
*Attorney, Agent, or Firm*—Oblon, Fisher, Spivak, McClelland & Maier

[57] ABSTRACT

A detergent composition containing at least one ampholytic surface active agent of $N^\epsilon$-long-chain-acyl-$N^\epsilon,N^\epsilon$-dimethyllysine or $N^\epsilon$-long-chain-acyl-$N^\alpha,N^\alpha,N^\alpha$-trimethyllysine or salt thereof represented by formula (I) or (II) below, and an anionic surface active agent. This detergent composition is superior in solubility, detergency, and sudsing on account of the synergistic effect of the two types of different components. This detergent composition exhibits high detergency in both soft water and hard water, and is mild to the skin and hair.

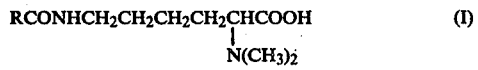

(I)

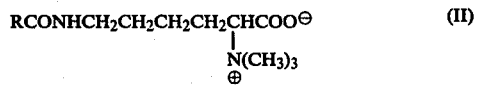

(II)

(where RCO denotes an aliphatic acyl group of carbon number 8 to 22.).

8 Claims, No Drawings

DETERGENT COMPOSITION COMPRISING A MIXTURE OF AN N-ACYLLYSINE AND ANIONIC SURFACE ACTIVE AGENTS, POSSESSING UNIQUE PROPERTIES IN SOFT AND HARD WATER

BACKGROUND OF THE INVENTION

1. Field of the Invention

The present invention relates to a new detergent composition which exhibits superior solubility, detergency, and sudsing not only in soft water but also in hard water, with mild action on the skin and hair, without causing discoloration.

2. Description of the Prior Art

Heretofore, anionic surface active agents which are widely used as the major component of detergent compositions have been supplied at a low price and used in large quantities. These anionic surface active agents are generally functionalized with sulfate groups, sulfoxyl groups, or carboxyl groups. Examples of these anionic surface active agents include: alkylsulfates, alkyl ether sulfates, alkylbenzenesulfonates, α-olefinsulfonates, sulfosuccinates, higher fatty acid salts, and N-acyl-neutral and acidic amino acid salts. Although these anionic surface active agents are widely used because of their superior sudsing and detergency in soft water and low price, they are useless in hard water where they form water-insoluble scum that contaminates objects being washed.

On the other hand, ampholytic surface active agents, which have both a cationic moiety and an anionic moiety per molecule, are superior in detergency, sudsing, and bacteriocidal and bacteriostatic action, as well as being mild to the skin and eyes. These agents exhibits these characteristics even in hard water. However, their cost makes them economically unattractive to use except in combination with anionic surface active agents.

Detergent composition made up of an ampholytic surface active agent and an anionic surface active agent possess the following merits. (1) The irritation caused by an anionic surface active agent is alleviated. (2) The bacteriocidal and bacteriostatic actions of an ampholytic surface active agent are maintained. (3) The sudsing performance of the composition exceeds that of the individual constituents component. (4) Usually, the critical miscelle concentration is low, and the surface active performance is accomplished at a low concentration. (5) The lack of detergent performance of anionic surface active agents in hard water is prevented to some extent.

According to Linfield, the ampholytic surface active agent, particularly that of the sulfobetaine type, is effective as a lime soap dispersing agent, as reported in "The Journal of the American Oil Chemist's Society", 55; 87 (1978). Despite the above-mentioned merits, detergent composition made up of ampholytic surface active agents and anionic surface active agents have not come into general use because various problems involving the ampholytic surface active agent remain to be solved.

Conventional ampholytic surface active agent are made of an alkylamine. The inevitable amine residues associated with alkylamines impairs the appearance of the product via discoloration. In rare cases, these amine causes allergy. Moreover, many of the conventional ampholytic surface active agents can form addition compounds with the anionic surface active agent, making it necessary to raise the temperature for dissolution.

The solution of a mixture of the two types of different surface active agents in certain mixing ratios exhibits viscoelastic properties. (Tsujii et al., The Journal of Physical Chemistry, Vol. 86, No. 8, p. 1437 (1982); and "Yukagaku", Vol. 29, No. 8, p. 562 (1980)).

Mixtures of ampholytic surface active agents and anionic surface active agents have low critical micelle concentrations. This phenomenon is accompanied by a rise in the dissolution temperature and, in some cases, by viscoelasticity (Fragrance Journal, 50; 56 (1981)). These phenomena indicate that in practical applications the mixture of an ampholytic surface active agent and anionic surface active agent yields a product which is not readily soluble in water and which does not exhibit detergency at low temperatures. Moreover, if the mixture is to be used in the form of liquid detergent composition, it will become solid or extremely viscous due to its viscoelasticity. Such a product is difficult to make and inconvenient to use.

For the above-mentioned reasons, detergent compositions made up of an ampholytic surface active agent and an anionic surface active agent have not been commercialized in spite of their inherent advantages.

SUMMARY OF THE INVENTION

In their studies on the application of basic amino acids to surface active agents, the present inventors found that derivatives of $N^\epsilon$-acyllysine having the following structure (I) and (II) can form a detergent composition which is free from the above-mentioned disadvantages. The present invention is based on this finding.

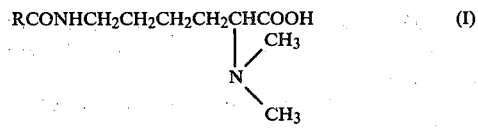

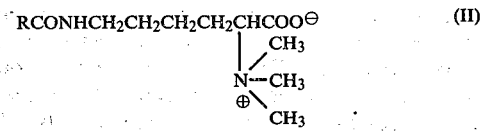

(where RCO denotes a $C_8$–$C_{20}$ saturated or unsaturated linear or branched aliphatic acyl group).

Thus, it is an object of this invention to provide a detergent composition made up of the above-mentioned compound and an anionic surface active agent having a $C_{10}$–$C_{18}$ hydrophobic group at a ratio of 1:9 to 9:1 by weight.

DETAILED DESCRIPTION OF THE INVENTION

The $N^\epsilon$-acyllysine derivative which is the ampholytic surface active agent constituting the detergent composition of this invention is a condensation product of $N^\alpha$,$N^\alpha$-dimethyllysine or $N^\alpha$,$N^\alpha$,$N^\alpha$-trimethyllysine, which is a basic amino acid, and a fatty acid. It does not inherently contain free amines, and therefore, the product of the invention is free of troublesome discoloration and allergy found in the conventional ampholytic surface active agent derived from an amine.

Table 1 shows the results of a test for discoloration that takes place after storage at high temperatures.

The detergent composition of this invention is composed chiefly of at least one of $N^\epsilon$-long chain-acyl-$N^\alpha$,-$N^\alpha$-dimethyllysine represented by formula (I) above or $N^\epsilon$-long chain-acyl-$N^\alpha,N^\alpha,N^\alpha$-trimethyllysine represented by formula (II) above or salts thereof, and an anionic surface active agent. This detergent composition has the following advantages.

TABLE 1

| | Storage at 50° C. | |
|---|---|---|
| Surface Active Agents | Initial | After 120 days |
| $N^\alpha$—dimethyl-$N^\epsilon$—lauroyllysine | No discoloration | No discoloration |
| $N^\alpha$—trimethyl-$N^\epsilon$—palmitoyllysine | No discoloration | No discoloration |
| Imidazoline-type ampholytic surface active agent (including salts) *1 | G-1 | G-2 |
| Imidazoline-type ampholytic surface active agent (excluding salts) *2 | G-3 | G-10 |
| Cocoamide betaine *3 | No discoloration | G-6 |
| Alkyl betaine *4 | No discoloration | No discoloration |

The degree of discoloration is indicated by the Gardner color scale.

Remarks:
*1: ENAGICOL C-40H, a product of Lion Corp.
*2: ENAGICOL CNS, a product of Lion Corp.
*3: LEVON 2000, a product of Sanyo Chemical Industries Ltd.
*4: AMPHITOL-24B, a product of Kao-Atlas Co., Ltd.

(1) It is much less irritating than the detergent composition based on an aninonic surface active agent alone.

(2) It is superior in sudsing and detergency to the detergent composition made of the individual constituent component.

(3) It exhibits a vastly superior performance at lower concentrations compared to conventional detergent compositions.

(4) Its activity and solubility are maintained in hard water.

Moreover, the detergent composition of this invention does not show viscoelasticity at any mixing ratio of the two components. The mixing of the two components results in a composition having a lower the dissolving temperature and an improved solubility. Moreover, this product is free from discoloration and an allergy caused by amines.

In other words, the detergent composition of this invention has overcome the disadvantages inherent in the conventional mixed detergent of an ampholytic surface active agent and an anionic surface active agent. Although some of the conventional detergent compositions have been improved in a certain aspect of performance (e.g., solubility in hard water, as disclosed in Japanese Patent Publication Nos. 30405/1977, 30406/1977, 30407/1977; and improvement of sudsing, as disclosed in Japanese Patent Laid-open No. 139614/1979), the detergent composition of this invention is the first to overcome all these disadvantages including discoloration and poor solubility in hard water.

The $N^\epsilon$-long chain-acyl-$N^\alpha,N^\alpha$-dimethyllysine or $N^\epsilon$-long chain-acyl-$N^\alpha,N^\alpha,N^\alpha$-trimethyllysine which is one component of the detergent composition of this invention has the above structural formulas (I) and (II). The former is disclosed in Japanese Patent Publication No. 11926/1967 as a substance having surface activity. It is also disclosed in Japanese Patent Publication No. 44172/1976 as a useful mildewcide. However, the fact that it forms an outstanding detergent composition when combined with an anionic surface active agent has not been disclosed.

On the other hand, the detergent composition containing the $N^\epsilon$-long chain-acyl-$N^\alpha,N^\alpha,N^\alpha$-trimethyllysine is not known, and the fact that it forms an outstanding detergent composition when combined with an anionic surface active agent has been disclosed for the first time in this invention.

The compounds (I) and (II) can be prepared by $N^\epsilon$-acylation of $N^\alpha,N^\alpha$-dimethyllysine and $N^\alpha,N^\alpha,N^\alpha$-trimethyl lysine with a $C_8$–$C_{22}$ fatty acid chloride and an alkali. This acylation is known as Schotten-Baumann reaction. The lysine derivatives may be optically active or racemic.

An $N^\epsilon$-acyl group of carbon number 8 to 22 is used. Such an acyl group includes, for example, 2-ethylhexanoyl, lauroyl, myristoyl, palmitoyl, stearoyl, oleoyl, isostearoyl, and other acyl groups of single fatty acid, and acyl groups of mixed fatty acid such as coconut oil fatty acid and hydrogenated tallow fatty acid.

The selection of compounds (I) and (II) depends on the type of the intended detergent composition. The latter is more soluble in water than the former, and the shorter the acyl group, the higher the solubility of the compounds. These compounds may be used individually or in combination.

These compounds have an isoelectric point in the neighborhood of neutral point. They are usually used at this isoelectric point; however, they are used in the form of sodium salt, potassium salt, ammonium salt, alkylolamine salt, and salt of basic amino acid if alkaline detergents are desirable, and they are used in the form of salts of hydrochloric acid, sulfuric acid, organic acid, and acidic amino acid if acidic detergents are desirable.

The other component of the detergent composition of this invention is an anionic surface active agent containing in its molecule a sulfate group, sulfoxyl group, or carboxyl group. It has a synergistic effect on the detergent composition. Such anionic surface active agents include, for example, alkylsulfate, alkyl ether sulfate, alkylbenzenesulfonate, α-olefinsulfonate, sulfosuccinate, higher fatty acid salt, N-acyl-neutral-amino acid salt, and N-acyl-acidic-amino acid salt. These anionic surface active agents have in the hydrophobic moiety of their molecule a skeleton made up of 10 to 18 carbon atoms. They also contain a cation such as lithium, potassium, sodium, ammonium, alkylolamine, and basic amino acid, which forms the salt. These anionic surface active agents are used individually or in combination for the detergent composition of this invention.

The blending ratio of the $N^\epsilon$-long-chain-acyl-lysine derivative (I) or (II) or salt thereof to the anionic surface active agent is 1:9 to 9:1 by weight, preferably 2:8 to 8:2 by weight, depending on the individual compositions.

The detergent compositions may be available in the form of solid, powder, paste, and liquid. They may be used for shampoo, cleansing foam, solid detergent, dish washing detergent, and liquid and solid detergent for clothes.

The detergent composition of this invention may be incorporated with other additives in such an amount that the essential characteristics of the detergent are not lost. Examples of such additives are as follows:

(1) Foam booster: fatty alkylol amide and amine oxide.

(2) Builder: organic salt such as citrate salt, glutamate salt, and pyrrolidone carboxylate salt; and inorganic salts such as sodium sulfate, sodium carbonate, phosphate salt, and zeolite.

(3) Emollient: protein, lanolin, glycerin, propylene glycol, ethylene glycol, polyethylene glycol, and 1,3-butylene glycol.

(4) Conditioner: cation-modified polymer and cationic surface active agent.

(5) Nonionic surface active agent: glycerin fatty acid ester, polyoxyalkylene glycerin fatty acid ester, sorbitan fatty acid ester, polyoxyethylene sorbitan fatty acid ester, sugar ester, and N-acyl amino acid long-chain alcohol ester.

(6) anti-dandruff: zinc pyrithione (7) Perfume and dye

The detergent composition of this invention as mentioned above has the following features.

(1) Available in a variety of forms such as paste, jelly, solid, and powder.

(2) Superior in sudsing, detergency, and solubility, even in hard water.

(3) Superior in sudsing and detergency even at low concentrations.

(4) Mild to the skin and hair.

(5) No discoloration.

The invention is now described with reference to the following examples, in which "%" means "wt%".

EXAMPLE 1

Detergent compositions were prepared by blending at various ratios $N^\epsilon$-long-chain-acyl-$N^\alpha,N^\alpha$-dimethyllysine or $N^\epsilon$-long-chain-acyl-$N^\alpha,N^\alpha,N^\alpha$-trimethyllysine and an anionic surface active agent. The resulting detergent compositions were evaluated with respect to solubility, sudsing, and detergency (for dish washing). The measuring conditions and results are as follows:

I. Measuring conditions:

(1) Solubility: 0.25% aqueous solution at room temperature and 40° C. In Table 2, S stands for "soluble" and SH stands for "turbid".

(2) Sudsing: 0.25% aqueous solution at 40° C., measured by Ross and Miles method.

(3) Detergency (dish washing): in accordance with method A described in "Yukagaku" 24, 596 (1975); at a concentration of 0.025%.

II. Results

The results are shown in Table 2. It is to be noted that the lysine derivative, one component of the detergent of this invention, exhibits superior sudsing and detergency even when used alone; but it produces a synergistic effect in solubility, sudsing, and detergency when combined with an anionic surface active agent.

TABLE 2

| Anionic surface active agent | Blending ratio Acyllysine derivative to anionic surface active agent | $N^\epsilon$—lauroyl-$N^\alpha,N^\alpha$—dimethyllysine | | | $N^\epsilon$—hydrogenated tallow fatty acid acyl-$N^\alpha,N^\alpha,N^\alpha$—trimethyllysine | | |
|---|---|---|---|---|---|---|---|
| | | Solubility | Sudsing (mm) | Detergency (No. of dishes) | Solubility | Sudsing (mm) | Detergency (No. of dishes) |
| — | 100:0 | S | 210 | 8.8 | S | 169 | 13.3 |
| Sodium lauryl sulfate | 75:25 | S | 232 | 11.6 | S | 184 | 16.0 |
| | 50:50 | S | 240 | 12.5 | S | 194 | 15.3 |
| | 25:75 | S | 233 | 8.0 | S | 205 | 10.5 |
| | 0:100 | S | 198 | 0.0 | S | 198 | 0.0 |
| Sodium polyoxyethylene lauryl sulfate | 75:25 | S | 227 | 9.5 | S | 200 | 13.5 |
| | 50:50 | S | 231 | 9.7 | S | 224 | 11.2 |
| | 25:75 | S | 225 | 7.0 | S | 223 | 7.0 |
| | 0:100 | S | 210 | 0.2 | S | 210 | 0.2 |
| Sodium linear-alkylbenzene-sulfonate (alkyl: $C_{12}$(75%) to $C_{14}$(25%)) | 75:25 | S | 220 | 11.6 | S | 207 | 13.8 |
| | 50:50 | S | 238 | 12.7 | S | 227 | 11.8 |
| | 25:75 | S | 230 | 8.0 | S | 223 | 7.4 |
| | 0:100 | S | 220 | 0.3 | S | 220 | 0.3 |
| Bar soap stock | 75:25 | S | 218 | 5.5 | S | 187 | 12.6 |
| | 50:50 | SH | 227 | 3.7 | SH | 209 | 10.9 |
| | 25:75 | SH | 237 | 3.7 | SH | 235 | 8.3 |
| | 0:100 | SH | 118 | 3.7 | SH | 118 | 3.7 |
| N—cocoyl glutamic acid monotriethanolamine salt | 75:25 | S | 234 | 9.7 | S | 212 | 13.8 |
| | 50:50 | S | 260 | 9.3 | S | 235 | 10.0 |
| | 25:75 | S | 322 | 6.0 | S | 245 | 6.5 |
| | 0:100 | S | 255 | 0.8 | S | 255 | 0.8 |

EXAMPLE 2

Mixtures of sodium lauryl sulfate (SLS) and $N^\epsilon$-lauroyl-$N^\alpha,N^\alpha$-dimethyllysine (I) and mixtures of sodium lauryl sulfate (SLS) and $N^\epsilon$-lauroyl-$N^\alpha,N^\alpha,N^\alpha$-trimethyllysine (II) were prepared and their dissolution temperatures were measured. The results are shown in Tables 3 and 4.

TABLE 3

| SLS/(I) | 100/0 | 80/20 | 70/30 | 60/40 | 50/50 | 40/60 | 30/70 | 20/80 | 0/100 |
|---|---|---|---|---|---|---|---|---|---|
| Dissolution temperature (°C.) | 14 | 8 | 3 | <0 | <0 | <0 | <0 | 24 | 39 |

TABLE 4

| SLS/(II) | 100/0 | 80/20 | 70/30 | 60/40 | 50/50 | 40/60 | 30/70 | 20/80 | 0/100 |
|---|---|---|---|---|---|---|---|---|---|
| Dissolu- | 14 | 3 | <0 | <0 | <0 | <0 | <0 | <0 | <0 |

TABLE 4-continued

| SLS/(II) | 100/0 | 80/20 | 70/30 | 60/40 | 50/50 | 40/60 | 30/70 | 20/80 | 0/100 |
|---|---|---|---|---|---|---|---|---|---|
| tion temperature (°C.) | | | | | | | | | |

Note:
SLS/(I), SLSL/(II): in molar ratio
concentration of mixture: 28 mol/l
dissolution temperature is a temperature at which the solution becomes clear when the solution is heated gradually.

The above results indicate that sodium lauryl sulfate and $N^\epsilon$-lauroyl-$N^\alpha,N^\alpha$-dimethyllysine and $N^\epsilon$-lauroyl-$N^\alpha,N^\alpha,N^\alpha$-trimethyllysine increase synergistically in solubility when mixed together, without the rise of dissolution temperature which is often the case with the known mixture of an ampholytic surface active agent and anionic surface active agent. In addition, the resulting mixture does not exhibit viscoelasticity at any mixing ratio. This suggests that the detergent composition of this invention is entirely different from the conventional detergent composition of similar type.

EXAMPLE 3

A 2:8 mixture of sodium lauryl sulfate (SLS) and $N^\epsilon$-lauroyl-$N^\alpha,N^\alpha$-dimethyllysine (I) was prepared and its dissolution temperatures in hard water was measured. The results are shown in Table 5.

TABLE 5

| Water | SLS alone | SLS/(I) = 2/8 |
|---|---|---|
| without CaCl$_2$ | 14° C. | 24° C. |
| with CaCl$_2$ (5 wt %) added | >100° C. | <0° C. |

Note:
Total concentration of mixture: 28 mol/l
The hardness corresponds to a U.S. hardness of 45,000 ppm.

This result indicates that SLS is comparatively soluble in soft water, but becomes almost insoluble in hard water. Not only does it lose detergency, but also it separates out to contaminate objects being washed. It is to be noted, however, that the detergent composition of this invention rather increases in solubility in hard water, which leads to improved detergency in hard water. This results suggests that the detergent composition of this invention will be useful in the hard water districts.

EXAMPLE 4

Liquid detergent compositions were prepared as follows, with the ratio of components (A) to (B) varied.

| | |
|---|---|
| 1:1 mixture of $N^\epsilon$—lauroyl-$N^\alpha,N^\alpha$—dimethyllysine and $N^\epsilon$—palmitoyl-$N^\alpha,N^\alpha,N^\alpha$—trimethyllysine (A) | } 20% |
| Sodium linear-alkylbenzenesulfonate (LAS) (alkyl group: C$_{12}$ (75%) to C$_{14}$ (25%)) (B) | |
| Calcium chloride hexahydrate (not added when LAS alone, but replaced by water) | 5% |
| Urea | 5% |
| Ethyl alcohol | 10% |
| Water | 60% |

The resulting detergent compositions were evaluated with respect to detergency (for dish washing) and skin irritation on rabbits. The results are shown in Table 6. It is noted that they are improved in detergency and the irritation by LAS is greatly alleviated.

TABLE 6

| Mixing ratio of acyllysine to LAS | 100/0 | 75/25 | 50/50 | 25/75 | 0/100 |
|---|---|---|---|---|---|
| Detergency (dish washing) | 13.0 | 14.0 | 13.2 | 9.0 | 2.0 |
| Skin irritation | 0.5 | 0.4 | 1.0 | 1.5 | 4.0 |

Measuring method:
Dish washing detergency: Same as in Example 1. Samples were prepared by dissolving 1.5 ml of the detergent composition in 1 liter of water.

Skin irritation test: Closed patch test using New Zealand white male rabbits weighing 2.5 to 3.0 kg, each group consisting of 6 heads. After one day, the sticking plaster was removed, and irritation was judged according to Draize standard. Samples were prepared by dissolving 25 ml of the detergent composition in 75 ml of water.

| Judgment | <2 | Mild |
|---|---|---|
| | 2-5 | Moderate |
| | >5 | Severe |

EXAMPLE 5

Shampoos were prepared as follows, with the ratio of components (A) to (B) varied.

| | |
|---|---|
| 2:1 mixture of $N^\epsilon$—cocoyl-$N^\alpha,N^\alpha$—dimethyllysine and $N^\epsilon$—lauroyl-$N^\alpha,N^\alpha,N^\alpha$—trimethyllysine (A) | } 20% |
| Sodium polyoxyetylenelaurylsulfate (LES) (B) | |
| Calcium chloride hexahydrate (not added when LES alone, but replaced by water) | 3% |
| Water | 77% |

The resulting shampoos were evaluated with respect to detergency (for hair washing) and feeling after washing, and skin irritation on rabbits. The results are shown in Table 7. It is noted that the shampoos are more improved in detergency, feeling after washing, and skin irritation than in the case where LES is used individually.

TABLE 7

| Mixing ratio of acyllysine to LES | 100/0 | 75/25 | 50/50 | 25/75 | 0/100 |
|---|---|---|---|---|---|
| Detergency (times of hair washings) | 4 | 4 | 4 | 5 | 6 |
| Skin irritation | 0.4 | 0.6 | 0.8 | 1.5 | 3.0 |

Measuring method:
Hair washing: 0.5 ml of sample shampoo was dropped onto a hairpiece soiled with 2 ml of artificial dirt and 0.05 g of clay. The hairpiece was washed by pressing for 15 seconds. In case of no sudsing, the hair piece was slightly rinsed in 1 liter of warm water which was not renewed, and the washing test was repeated after swishing. When sudsing took place, the number of droppings of shampoo was recorded. The small values indicate high detergency.

Skin irritation test: Same as in Example 4. Samples were prepared by diluting 25 ml of shampoo with 75 ml of water.

EXAMPLE 6

A shampoo was prepared from the following components.

| | |
|---|---|
| $N^\epsilon$—lauroyl-$N^\alpha,N^\alpha$—dimethyllysine | 5% |
| $N^\epsilon$—lauroyl-$N^\alpha,N^\alpha,N^\alpha$—trimethyllysine | 4% |
| N—cocoyl glutamate monotriethanolamine | 3% |
| Fatty acid amide ether sulfate (Sunamide C-3, a product of Nippon Oils & Fats Co., Ltd.) | 4% |
| Lauryl sulfate triethanolamine | 4% |
| Coconut oil fatty acid diethanolamide | 2% |
| Polyoxyethylene (20) cetyl ether | 1.5% |
| Glycerin | 2% |
| Disodium citrate | 2% |
| PRODEW #100 (humectant, a product of Ajinomoto Co., Inc.) | 3% |
| Cationic cellulose | 0.5% |
| Water | 69% |

The resulting shampoo was found to be mild to the hair and skin, to foam well and persist in sudsing, and to have good feel after use.

EXAMPLE 7

A paste detergent for toilet use was prepared from the following components.

| | |
|---|---|
| $N^\epsilon$—hydrogenated tallow fatty acid acyl-$N^\alpha,N^\alpha$—dimethyllysine | 10% |
| $N^\epsilon$—hydrogenated tallow fatty acid acyl-$N^\alpha,N^\alpha,N^\alpha$—trimethyllysine | 7% |
| Potassium myristate | 14% |
| Potassium stearate | 6% |
| Lauroyl collagen protein hydrolyzate | 3% |
| Glycerin | 5% |
| Polyethylene glycol #600 | 10% |
| Water | 45% |

The resulting paste detergent was found to be mild to the skin and superior in sudsing.

EXAMPLE 8

A transparent jelly detergent for toilet use was prepared from the following components.

| | |
|---|---|
| $N^\epsilon$—cocoyl-$N^\alpha,N^\alpha$—dimethyllysine | 20% |
| Sodium laurate | 20% |
| Glycerin | 5% |
| AJIDEW N-50 (humectant, a product of Ajinomoto Co., Inc.) | 3% |
| Water | 52% |

The resulting jelly detergent was found to be weakly alkaline and superior in sudsing and transparency.

EXAMPLE 9

A transparent jelly detergent for toilet use was prepared from the following components.

| | |
|---|---|
| $N^\epsilon$—lauroyl-$N^\alpha,N^\alpha$—dimethyllysine | 14% |
| Monosodium N—cocoylglutamate | 25% |
| Coconut oil fatty diethanol amide | 10% |
| Glycerin | 4% |
| Water | 47% |

The resulting jelly detergent was found to be weakly acidic and superior in sudsing and feel after use.

EXAMPLE 10

A transparent jelly detergent for toilet use was prepared from the following components.

| | |
|---|---|
| $N^\epsilon$—lauroyl-$N^\alpha,N^\alpha$—dimethyllysine | 17% |
| $N^\epsilon$—palmitoyl-$N^\alpha,N^\alpha,N^\alpha$—trimethyllysine | 3% |
| Sodium $\alpha$-olefin sulfonate | 8% |
| Sodium lauryl sulfate | 12% |
| Propylene glycol | 3% |
| Water | 57% |

The resulting jelly detergent was found to be neutral and superior in sudsing and transparency.

EXAMPLE 11

Detergent bars were prepared from the following components, with the ratio of acyllysine derivative to sodium N-acylglutamate varied.

| | |
|---|---|
| 1:1 mixture of $N^\epsilon$—lauroyl-$N^\alpha,N^\alpha$—dimethyllysine and $N^\epsilon$—hardened beef tallow fatty acid acyl-$N^\alpha,N^\alpha$—dimethyllysine Monosodium N—acylglutamate* | 84% |
| Cetyl alcohol | 6% |
| N—lauroyl glutamate distearyl ester | 2% |
| Water | 8% |

*(Acyl group is composed of half-hardened tallow beef fatty acid and coconut oil fatty acid at a ratio of 8:2.)

The above components were thoroughly mixed using a small roll mill, and resulting mixture was extruded into bar soap using a laboratory machine with the die kept at 40° to 50° C. The bar soap stock was then molded using a foot-operated molder. The performance of the resulting soap is shown in Table 8.

It is to be noted that the synergistic effect of mixing the two types of different surface active agents is pronounced in sudsing and shape retention. In addition, it is noted that the addition of N-acyllysine derivatives overcomes the disadvantage of N-acylglutamate detergent bars of sticking to a soap case.

TABLE 8

| | Ratio of acyllysine derivative to acyl glutamate | | |
|---|---|---|---|
| Performance | 100/0 | 50/50 | 0/100 |
| Sudsing*1 | 240 | 250 | 190 |
| Solubility by*2 rubbing | 46 | 43 | 50 |
| Dissolution and*3 disintegration | +3.0 | +5.0 | −15.6 |
| Hardness*4 | 90 | 87 | 85 |
| Release from*5 | Good | Good | Poor |

TABLE 8-continued

| Performance | Ratio of acyllysine derivative to acyl glutamate | | |
|---|---|---|---|
| | 100/0 | 50/50 | 0/100 |
| soap case | | | |

Measuring methods:
*¹In accordance with JIS K3362-1970. Concentration 0.25%, temperature 40° C., 0-minute value.
*²In accordance with JIS K3304-1956.
*³Weight increase in percent that took place when the detergent bar was suspended in water at 20° C. for 1 hour.
*⁴In accordance with JIS Z2246, with a Shore A hardness meter.
*⁵The detergent bar (3.5 × 5.0 × 1.0 cm) was placed overnight in a soap case containing 1 ml of water, and thereafter the detergent bar was removed from the soap case.

EXAMPLE 12

A solid detergent was prepared from the following components as in Example 11.

| | |
|---|---|
| $N^\epsilon$—hydrogenated tallow fatty acid acyl-$N^\alpha,N^\alpha$—dimethyllysine | 45% |
| Toilet soap stock (water content 8%) | 23% |
| Behenyl alcohol | 5% |
| α-Sulfofatty acid ester salt (Sunbase powder, a product of Nippon Oils & Fats Co., Ltd.) | 10% |
| N—Methyl-N—oleoyltaurine sodium | 10% |
| Water | 7% |

The resulting solid detergent was found to be superior in sudsing and detergency, with formation of very little scum in hard water.

EXAMPLE 13

A powder detergent for clothes washing was prepared from the following components.

| | |
|---|---|
| $N^\epsilon$—hydrogenated tallow fatty acid acyl-$N^\alpha,N^\alpha,N^\alpha$—trimethyllysine sodium | 9% |
| Sodium secondary alkanesulfonate | 3% |
| Sodium linear alkylbenzenesulfonate (alkyl: $C_{12}$ 75% and $C_{14}$ 25%) | 10% |
| Sodium dioctyl sulfosuccinate | 2% |
| Sodium tripolyphosphate | 10% |
| Sodium metasilicate | 22% |
| Anhydrous sodium sulfate | 43% |
| Sodium carboxymethyl cellulose | 1% |

The resulting powder detergent was found to be superior in detergency.

REFERENTIAL EXAMPLE

Preparation of $N^\epsilon$-lauroyl-$N^\alpha,N^\alpha,N^\alpha$-trimethyllysine 10 Grams of $N^\epsilon$-lauroyl-$N^\alpha,N^\alpha$-dimethyllysine methylester was dissolved in 50 ml of methanol with stirring. To this solution was added dropwise 7.7 g of methyl iodide at room temperature and stirred for 3 hours. Then, the stirring was continued at 55° C. for 2 hours.

The reaction solution was concentrated under reduced pressure to dryness. To the residue was added 30 ml of methanol and heated to 40° C. whereby the residue was dissolved in methanol. After the addition of 165 ml of ethylethyl, the solution was allowed to stand overnight. The precipitated crystals were filtered out and dried to obtain 13.4 g of pale yellowish crystals of $N^\epsilon$-lauroyl-$N^\alpha,N^\alpha,N^\alpha$-trimethyllysine methylester iodide (yield: 96.8%).

12.3 Grams of $N^\epsilon$-lauroyl-$N^\alpha,N^\alpha,N^\alpha$-trimethyllysine methylester iodide was dissolved in 50 ml of methanol with stirring and 72.3 ml of 1N aqueous solution hydroxide solution was added thereto. The solution was heated at 40° C. for 2 hours and then heated at 60° C. for 2.5 hours. After cooling to room temperature, the solution was adjusted to pH 3–4 with hydrochloric acid and diluted with methanol to be sodium concentration of 0.2 mol/l. The solution was treated with 200 ml of strongly acidic ion exchange resin (H-form) to adsorp sodium and $N^\epsilon$-lauroxy-$N^\alpha,N^\alpha,N^\alpha$-trimethyllysine thereon. The exchange resin was washed with methanol and treated with 2.0 l of 3N-aqueous ammonia-methanol solution. The eluted solution was concentrated under reduced pressure. Butanol was added to the residue and concentrated under reduced pressure to remove water. A similar concentration procedure was reeated to obtain 7.62 g $N^\epsilon$-lauroyl-$N^\alpha,N^\alpha,N^\alpha$-trimethyllysine, yield 85.4%. The product was recrystallized from methanol/ethyl ether.

What is claimed is:
1. A detergent composition comprising
   (a) at least one of $N^\epsilon$-long-chain-acyl-$N^\alpha,N^\alpha$-dimethyllysine of the formula

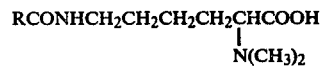

or $N^\epsilon$-long-chain-acyl-$N^\alpha,N^\alpha,N^\alpha$-trimethyllysine of the formula

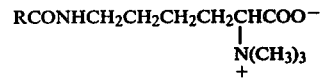

or a salt thereof, wherein RCO represents an aliphatic alkanoyl group of carbon number 8–22, and
   (b) an anionic surface active agent having a hydrophobic group of carbon number 10 to 18, wherein components (a) and (b) are present at a ratio of 1:9 to 9:1 by weight.

2. A detergent composition as claimed in claim 1, wherein the anionic surface active agent is a $C_{10}$–$C_{18}$ alkylsulfate or $C_{10}$–$C_{18}$ alkyl ether sulfate.

3. A detergent composition as claimed in claim 1, wherein the anionic surface active agent is a $C_{10}$–$C_{18}$ alkylbenzenesulfonate or $C_{10}$–$C_{18}$ α-olefinsulfonate.

4. A detergent composition as claimed in claim 1, wherein the anionic surface active agent is a sodium salt of $C_{10}$–$C_{18}$ higher fatty acid.

5. A detergent composition as claimed in claim 1 wherein said salt is a sodium salt, potassium salt, ammonium salt, alkylamine salt, hydrochloric acid salt, sulfuric acid salt, or organic acid salt.

6. A detergent composition as claimed in claim 1 wherein RCO is lauroyl, palmitoyl, cocoyl, hydrogenated-tallow-fatty-acid-acyl or hardened-beef-tallow-fatty-acid-acyl.

7. A detergent composition as claimed in claim 1 wherein component (a) has at least one of said formulas and is not a salt therof.

8. A detergent composition as claimed in claim 6 wherein component (a) has at least one of said formulas and is not a salt therof.

* * * * *